United States Patent [19]

Gaylord, Jr. et al.

[11] 4,235,228
[45] Nov. 25, 1980

[54] ORTHOPEDIC CAST MATERIAL

[75] Inventors: John F. Gaylord, Jr.; John F. Gaylord, III, both of Matthews, N.C.

[73] Assignee: Medical Specialties, Inc., Charlotte, N.C.

[21] Appl. No.: 61,371

[22] Filed: Jul. 27, 1979

[51] Int. Cl.³ .............................................. A61F 5/04
[52] U.S. Cl. .................................................. 128/91 R
[58] Field of Search ........................ 128/83, 87–91 R, 128/92 R, 93

[56] References Cited

U.S. PATENT DOCUMENTS

| | | | |
|---|---|---|---|
| 2,960,984 | 11/1960 | Parker | 128/91 R |
| 3,826,252 | 7/1974 | Laico | 128/91 R |
| 3,882,857 | 5/1975 | Woodall, Jr. | 128/90 |
| 3,900,024 | 8/1975 | Lauber et al. | 128/91 R |
| 3,923,049 | 12/1975 | Lauber et al. | 128/91 R |
| 4,126,130 | 11/1978 | Cowden et al. | 128/91 R |

*Primary Examiner*—C. Fred Rosenbaum
*Attorney, Agent, or Firm*—Bell, Seltzer, Park & Gibson

[57] ABSTRACT

A unitary orthopedic cast material is provided which comprises a layer of plaster splint material, a relatively thick padding layer on one side of the plaster splint material, and a resilient covering fabric enclosing the plaster splint layer and the padding layer. The padding layer and covering fabric are each fabricated from a hydrophobic textile material, such as polypropylene fibers, which acts to wick moisture from the skin of the wearer to the outer surface of the cast material, where the moisture readily evaporates, to thereby alleviate skin irritation and odor beneath the cast.

14 Claims, 9 Drawing Figures

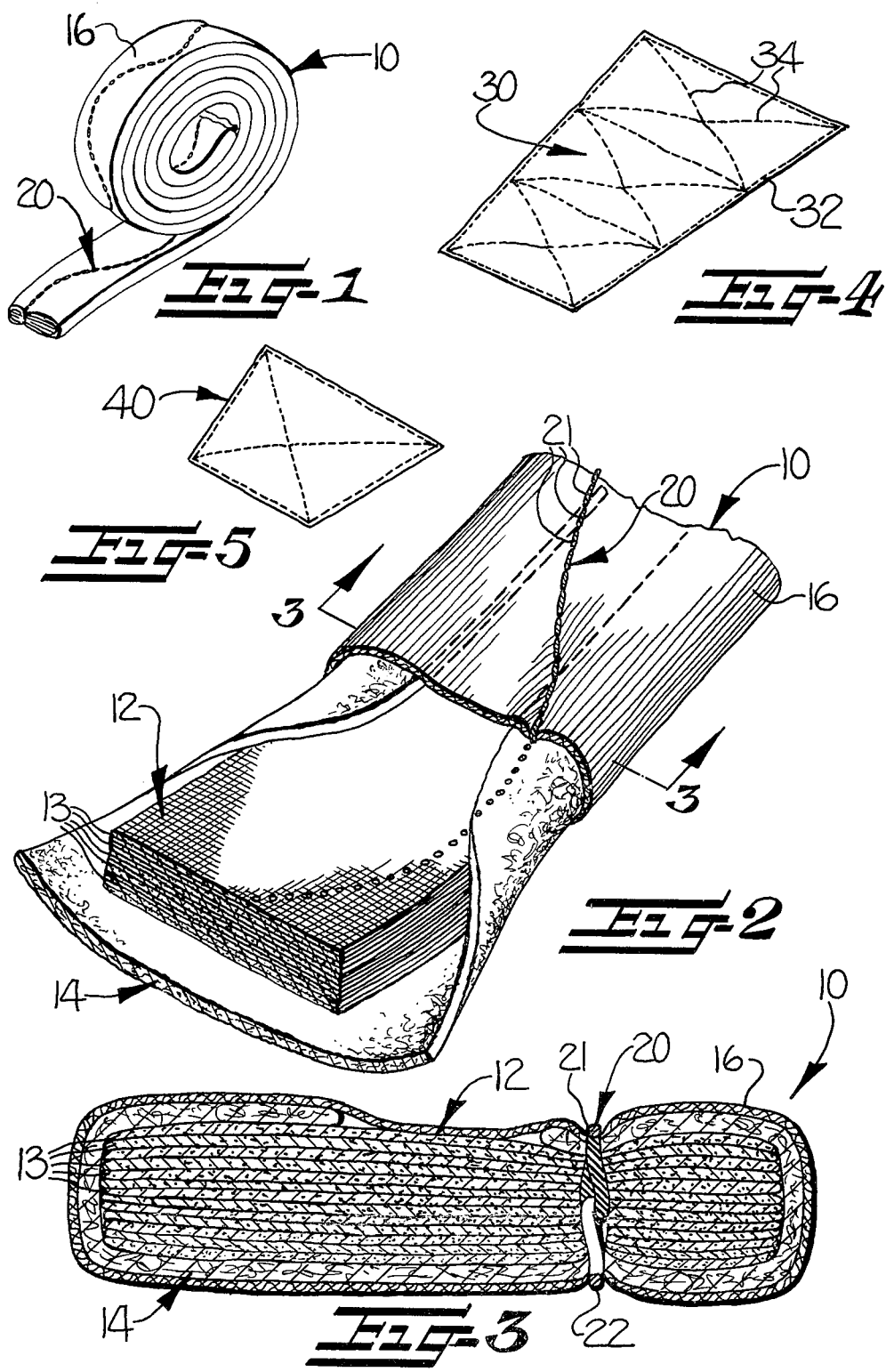

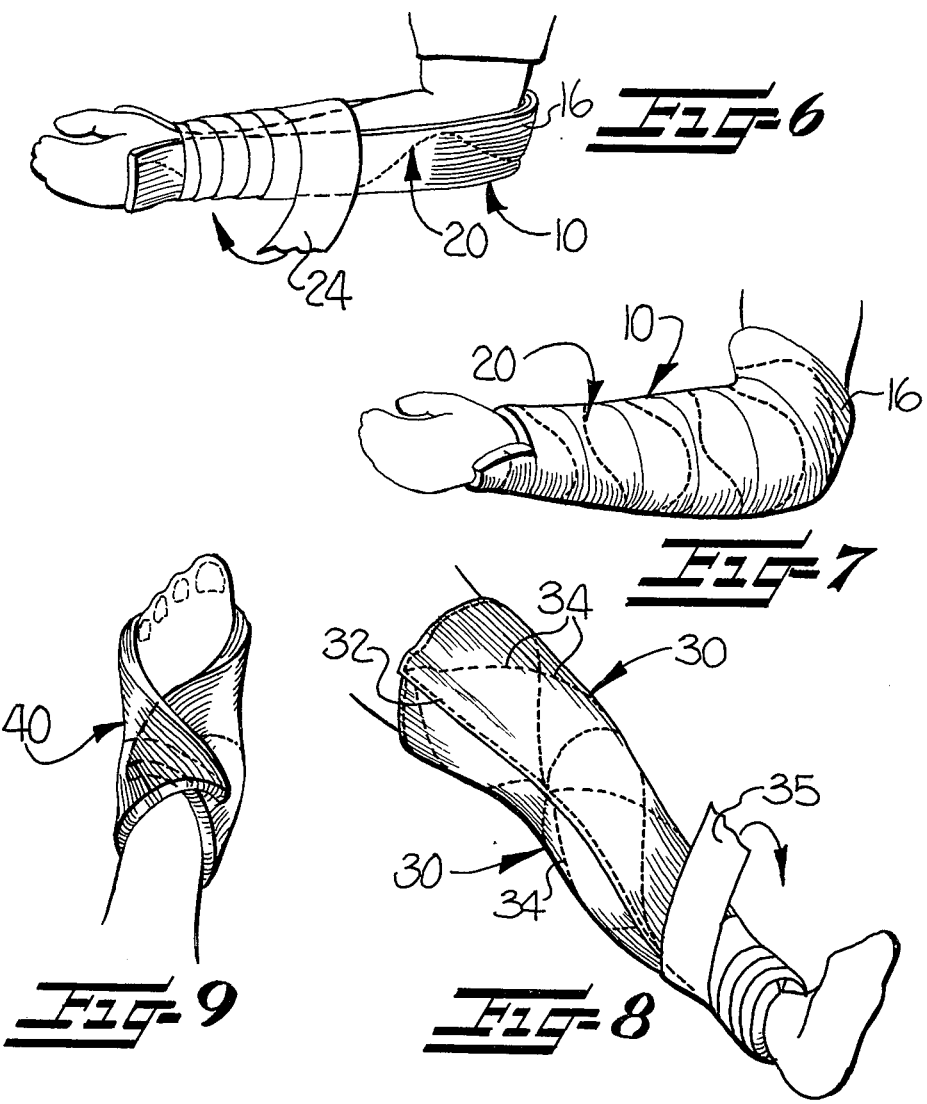

ORTHOPEDIC CAST MATERIAL

The present invention relates to an orthopedic cast material, and more particularly, to a prepadded, unitized cast material which is characterized by the ability to be quickly applied, and improved comfort to the wearer.

For many years, it has been conventional practice to fabricate a cast upon an injured limb by initially applying a protective covering of cotton fabric or the like, and then overwrapping the covering and limb with a wetted casting material consisting of a woven cloth impregnated with plaster of Paris. While the above conventional plaster of Paris casting system is in widespread use, it possesses several significant and well recognized disadvantages. Specifically, the application procedure is messy and time consuming, several components are required, and considerable skill is necessary for the proper application of the cast. Still further, the cast is substantially impermeable to the passage of ventilating air and moisture. Thus the heat and perspiration from the body of the wearer are trapped beneath the cast, resulting in general discomfort from the heat, skin irritation, and an unpleasant odor.

In order to alleviate the above disadvantages of the conventional orthopedic cast a unitary cast material has recently been proposed which comprises several sheets of plaster splint material enclosed between a cellular foam layer on one side and a flannel fabric on the other side. In use, the entire casting material is wetted, and then applied to the limb with the foam being positioned against the body for padding purposes. A unitary casting material of this type is further disclosed in U.S. Pat. Nos. 3,900,024 and 3,923,049. While such unitary casting material is seen to alleviate certain of the problems associated with the application of the above conventional casting system, it is not totally satisfactory since the foam layer would inherently serve as an insulating barrier to heat and moisture, and would thus hold the heat and perspiration against the skin. Accordingly, it is believed that the foam layer of this unitary system would aggrevate the discomfort from the heat and perspiration, as compared to the conventional cast.

It is accordingly an object of the present invention to provide a unitary orthopedic cast material which effectively overcomes the above deficiencies of the present cast systems.

It is a more particular object of the present invention to provide a prepadded, unitary cast material which may be quickly applied, with little mess, and which requires less skill for its proper application.

It is also an object of the present invention to provide a prepadded, unitary cast material which tends to wick moisture from the skin of the wearer to thereby facilitate the evaporation of the moisture, and thus reduce the heat held beneath the cast and alleviate skin irritation and odor.

It is a further object of the present invention to provide a prepadded, unitary cast material in which an anti-microbial agent may be readily incorporated to reduce the development of odor causing organisms.

These and other objects and advantages of the present invention are achieved in the embodiments illustrated herein by the provision of a cast material which comprises a layer of plaster splint material, a relatively thick padding layer of hydrophobic textile material overlying at least one side of the plaster splint layer, and a resilient covering fabric composed of hydrophobic textile material enclosing the plaster splint layer and the padding layer, to thereby maintain the assembly thereof. Preferably, each of the padding layer and covering fabric consist essentially of a non-wetting polymeric material, such as polypropylene fibers. In one embodiment, the cast material has an elongate, relatively narrow configuration, which may be severed to a desired length at the time of application, and in another embodiment, the cast material is in a generally rectangular or sheet form which is applied as a unit.

Some of the objects having been stated, other objects will appear as the description proceeds, when taken in connection with the accompanying drawings, in which FIG. 1 is a perspective view of an elongate strip of cast material embodying the present invention, and illustrating the same in wound roll form to facilitate shipment and storage;

FIG. 2 is an enlarged perspective view of the cast material of FIG. 1, with portions broken away to illustrate the interior construction;

FIG. 3 is a sectional view taken substantially along the line 3—3 of FIG. 2;

FIG. 4 is a perspective view of a second embodiment of the invention, and wherein the cast material is in the form of a relatively large trapezoidal sheet;

FIG. 5 is a perspective view of still another embodiment, and wherein the cast material is in the form of a smaller trapezoidal sheet;

FIG. 6 is a perspective view of the cast material of FIG. 1, shown being applied to a patient's arm in the manner of a "sugar-tong" splint;

FIG. 7 is a perspective view of the cast material of FIG. 1, shown being applied to a patient's arm in a helically wrapped arrangement;

FIG. 8 is a perspective view showing two sheets of the cast material of FIG. 4 applied as anterior and posterior splints on the leg of a patient; and FIG. 9 is a perspective view of the cast material of FIG. 5, shown being applied about the ankle of a patient.

Referring more specifically to the drawings, FIGS. 1–3 illustrate an embodiment of the present invention which comprises a cast material 10 which is in the form of a elongate, relatively narrow strip. The material 10 typically is about three to four inches wide, and has an original length of about twenty feet. It is preferably packaged in wound roll form as shown in FIG. 1, to facilitate shipment and storage. In use, a suitable length of the material 10 is severed from the roll, wet by dipping in water, and positioned directly on the patient in the manner hereinafter further described.

As best seen in FIG. 2, the cast material 10 comprises a layer 12 composed of a plurality of sheets 13 of plaster splint material, a padding layer 14 composed of a sheet of non-woven textile material, and a tubular covering fabric or stockinet 16 enclosing the splint layer and padding layer, to thereby maintain their assembly.

The sheets 13 of the plaster splint material are of the type conventionally used to form an orthopedic cast, and they typically comprise a gauze or similar fabric material impregnated with plaster of Paris.

The non-woven sheet of the padding layer 14 consists of a hydrophobic textile material, and preferably comprises a non-woven sheet of a non-wetting polymeric soft fibrous material, such as a non-woven mat of relatively fine polypropylene fibers. As illustrated, a single padding sheet is utilized which has a width sufficient to extend about the two longitudinal side edges of the splint layer 12 and overlie the adjacent portion only of the upper side thereof. Thus the padding layer overlies essentially only one side of the plaster splint layer, and the other or upper side is predominantly free of an overlying padding layer. This arrangement serves to provide adequate padding along the bottom side and edges of the cast material, while minimizing the amount of padding material required.

As a specific example, the padding layer 14 may have a thickness of about one eighth inch, a density of between 3.5 to 5.5 ounces per square yard (or about six pounds per cubic foot) and a polypropylene fiber size of 3 denier. Alternatively, the layer 14 could comprise a plurality of sheets of such non-woven material, where additional softness and wicking action as described below is desirable.

The tubular stockinet 16 is preferably of a resilient, knit fabric construction, with the yarns being formed of a non-wetting polymeric material, such as polypropylene. Thus in accordance with the present invention, the padding layer 14 and resilient covering stockinet 16 are each fabricated from hydrophobic materials, and it has been found that such materials act to wick moisture away from the skin of the wearer. More particularly, the wicking action of these materials not only tends to separate and isolate the moisture from the skin, but also it appears that the moisture is conveyed around the padded side edges to the outer surface of the cast material, where the moisture readily evaporates. Thus evaporation of the perspiration is facilitated, which in turn serves to maintain the underlying skin in a relatively dry, cool, and odor-free condition. Also, such materials permit the passage of ventilating air to the underlying skin to further contribute to the drying and cooling thereof. Polypropylene is preferred for use with the present invention for the further reasons that it has low flammability, is not abrasive to the skin, and does not support the growth of mildew or fungi.

The use of the above-described polymeric materials in forming the padding layer and covering fabric results in a further significant advantage, in that it has been found that an anti-microbial agent may be topically applied to or incorporated directly into such materials, and that the development of bacteria on the skin beneath the cast may thereby be retarded. As a specific example, it has been found that the anti-microbial agent having the USAN non-proprietary name of Triclosan (2, 4, 4'-Trichloro-2'-Hydroxydiphenyl Ether) may be incorporated directly into the resin mixture of polypropylene in amounts between about 1% to 5% by weight, and prior to its formation into fibers. The anti-microbial agent is thereby intimately admixed in the composition of the resulting fibers.

To maintain the assembly of the various components of the cast material 10, there is further provided a line of sinusoidal stitching 20 which extends along the longitudinal length of the material. The sinusoidal configuration of the stitching 20 is preferred to a straight line, since the latter configuration tends to form a fold line along the center of the material, which can result in undue flexibility. Also, the sinusoidal configuration permits the stitching to engage and support the edges of the padding layer on the outer side of the plaster splint material as seen in FIG. 2.

It is also preferred that the two threads 21, 22 forming the stitching 20 be of differing colors, with the thread of one color being visible on one side of the material 10 and the other thread being visible on the other side. The differing colors of the two threads serves to visually distinguish the two sides of the cast material, and thereby serves to readily identify and distinguish the padded side from the non-padded side. This in turn facilitates the application of the cast material with the padded side adjacent the body of the patient, and appropriate instructions may be provided to the physician to position the cast material on the body with the thread of the color of thread 21 positioned outwardly.

The cast material 10 may be applied to the patient in a number of differing configurations. In each case, however, a suitable length of the material is initially withdrawn and severed from the supply roll, and the severed length is briefly immersed in warm water. Next, any excess water is squeezed out, and the material is then placed on a flat surface and smoothed by hand to intermix and meld the plaster splint layers. The material is then ready to be applied directly to the limb of the patient. As shown in FIG. 6, the cast material 10 is applied in the manner of a "sugar-tong" splint to the forearm of a patient. A conventional cast wrap 24 may then be wrapped helically about the limb and cast material, to hold the same in place. After a few minutes, the cast material will have set up, to form a stable orthopedic cast. In FIG. 7, the cast material 10 is shown wrapped helically about the injured limb. If desired, a cast wrap may also be disposed about the cast as shown in FIG. 7 to aid in maintaining the helical configuration and positioning of the material.

FIG. 4 illustrates at 30 another embodiment of a cast material which embodies the present invention. The cast material 30 is in the form of a four-sided, trapezoidal sheet which can range in size depending upon the particular limb to which it is to be applied, as well as the size of the patient. Typically, however, the cast material 30 is about two feet in length by one foot in width.

The cast material 30 is similar in construction to the material 10, and comprises a similar layer of plaster splint material, and a similar layer of padding. Also, the padding layer will preferably extend about the two side edges of the splint material to facilitate wicking as is the case with the material 10. The outer covering fabric of the material 30 may comprise separate upper and lower knit fabric sheets which are stitched together along the peripheral edges as indicated at 32 in FIG. 4, or the covering fabric could alternatively comprise a single sheet which is folded along one of the edges, with the remaining edges being stitched. In any case however, the four side edges of the covering fabric are closed so as to totally enclose the layer of plaster splint material and padding layer therewithin. Also, several lines of stitching 34 may extend across the material in an X-shaped arrangement to maintain the positioning of the various components and as shown in FIG. 4.

As one example of use, the cast material 30 may be used alone to form a posterior splint on a leg, with a cast wrap being wound about the cast and leg to hold the cast in place. Where added support is required, a second sheet of cast material 30 may be positioned anteriorly on the leg and as shown in FIG. 9, and the two members held together by the cast wrap 35.

The cast material 40 as illustrated in FIG. 5 is in the form of a smaller trapezoidal sheet, but is otherwise similar in construction to the sheet of cast material 30. The smaller sheet 40 is typically used as an ankle cast as shown in FIG. 8, and if desired, the cast material 40 may be overwrapped with a cast wrap to aid in holding the cast in its desired configuration while being worn.

While various configurations of the cast material of the present invention have been illustrated and described herein, it will be appreciated that other configurations and sizes are possible, and may be desirable for certain end uses.

In the drawings and specification, there has been set forth a preferred embodiment of the invention, and although specific terms are employed, they are used in a generic and descriptive sense only and not for purposes of limitation.

That which is claimed is:

1. A prepadded, unitized orthopedic cast material characterized by the ability to be quickly applied, and improved comfort to the wearer, and comprising
   a layer of plaster splint material,
   a relatively thick padding layer comprising a hydrophobic textile material overlying at least one side of said plaster splint layer, and
   a covering fabric comprising a hydrophobic textile material enclosing said plaster splint layer and said padding layer, to thereby maintain the assembly thereof.

2. The orthopedic cast material as defined in claim 1 wherein said hydrophobic textile material of each of said padding layer and said covering fabric consists essentially of a non-wetting polymeric material.

3. The orthopedic cast material as defined in claim 2 wherein said padding layer comprises at least one sheet of a non-woven fabric.

4. The orthopedic cast material as defined in claim 3 wherein said covering fabric is of a resilient knit construction.

5. The orthopedic cast material as defined in claim 4 wherein said layer of plaster splint material comprises a plurality of superposed sheets for such material.

6. The orthopedic cast material as defined in claim 1 wherein said hydrophobic textile material of each of said padding layer and resilient covering fabric consists essentially of polymeric fibers having an antimicrobial agent carried thereby.

7. The orthopedic cast material as defined in claim 1 wherein said padding layer overlies one side and the two longitudinal side edges of said plaster splint layer.

8. The orthopedic cast material as defined in claim 1 wherein said cast material is of a four-sided configuration in plan view, and wherein the four side edges of said covering fabric are closed so as to totally enclose the layer of plaster splint material and padding layer therewithin.

9. A prepadded, unitized orthopedic cast material characterized by the ability to be quickly applied, and improved comfort to the wearer, and comprising
   a plurality of superposed sheets of plaster splint material,
   a relatively thick padding layer of non-woven hydrophobic textile material overlying at least one side of said sheets of plaster splint material, and
   a tubular stockinet of resilient hydrophobic knit fabric material enclosing said sheets of plaster splint material and said padding layer, to thereby maintain the assembly thereof.

10. The orthopedic cast material as defined in claim 9 wherein said cast material is of elongate, relatively narrow configuration, and further includes a line of sinusoidal stitching extending along the longitudinal length thereof.

11. The orthopedic cast material as defined in claim 10 wherein said padding layer overlies one side, the two longitudinal side edges, and a portion only of the other side, of said plaster splint material.

12. The orthopedic cast as defined in claim 11 wherein said sinusoidal line of stitching engages at longitudinally spaced locations said portion of said padding overlying said other side of said plaster splint material.

13. The orthopedic cast material as defined in claim 11 wherein said sinusoidal line of stitching comprises threads of differing color, with the thread of one color being visible on one side of the cast material and the other thread being visible on the other side, whereby the thread colors serve to distinguish the two sides of the cast material and thereby facilitate its application with the padded side adjacent the body of the patient.

14. The orthopedic cast material as defined in claim 9 wherein said padding layer and said stockinet each consist essentially of polypropylene fibers having an anti-microbial agent intimately admixed therein.

* * * * *